(12) United States Patent
Chipman et al.

(10) Patent No.: US 7,657,331 B2
(45) Date of Patent: Feb. 2, 2010

(54) PROCESS AND SYSTEMS FOR THE EPOXIDATION OF AN OLEFIN

(75) Inventors: Peter Ingraham Chipman, Houston, TX (US); Jeffrey Michael Kobe, Katy, TX (US); Arjan Jan Te Raa, Dordrecht (NL); Leonid Isaakovich Rubinstein, Houston, TX (US); Brian Scott Vanderwilp, Katy, TX (US); Thijs Wermink, Voorschoten (NL)

(73) Assignee: Shell Oil Company, Houston, TX (US)

( * ) Notice: Subject to any disclaimer, the term of this patent is extended or adjusted under 35 U.S.C. 154(b) by 367 days.

(21) Appl. No.: 11/670,335

(22) Filed: Feb. 1, 2007

(65) Prior Publication Data

US 2007/0129557 A1 Jun. 7, 2007

Related U.S. Application Data

(60) Division of application No. 10/404,829, filed on Apr. 1, 2003, now Pat. No. 7,193,094, which is a continuation-in-part of application No. 10/299,878, filed on Nov. 19, 2002, now abandoned.

(60) Provisional application No. 60/331,828, filed on Nov. 20, 2001.

(51) Int. Cl.
    *G05B 13/00* (2006.01)
(52) U.S. Cl. .................................. 700/28; 549/536
(58) Field of Classification Search .................. 700/28; 549/536
    See application file for complete search history.

(56) References Cited

U.S. PATENT DOCUMENTS

| | | | |
|---|---|---|---|
| 2,279,470 A | 4/1942 | Law et al. .................. 260/348 |
| 3,962,285 A | 6/1976 | Cusumano ............ 260/348.5 R |
| 4,055,579 A | 10/1977 | Cocuzza et al. ......... 260/348.34 |
| 4,761,394 A | 8/1988 | Lauritzen .................... 502/348 |
| 4,766,105 A | 8/1988 | Lauritzen .................... 502/216 |
| 4,808,738 A | 2/1989 | Lauritzen .................... 549/536 |
| 4,810,689 A | 3/1989 | Hayden ....................... 502/347 |
| 4,820,675 A | 4/1989 | Lauritzen .................... 502/216 |
| 4,822,900 A | 4/1989 | Hayden ....................... 549/534 |
| 4,829,044 A | 5/1989 | Boxhoorn et al. .......... 502/348 |
| 4,831,162 A | 5/1989 | Nakajima et al. .......... 549/534 |
| 4,833,261 A | 5/1989 | Lauritzen .................... 549/536 |
| 4,845,296 A | 7/1989 | Ahmed et al. .............. 564/477 |
| 4,874,739 A | 10/1989 | Boxhoorn ................... 502/218 |
| 4,874,879 A | 10/1989 | Lauritzen .................... 549/536 |
| 4,908,343 A | 3/1990 | Bhasin ....................... 502/218 |
| 4,950,773 A | 8/1990 | Monnier et al. ............ 549/534 |
| 5,011,807 A | 4/1991 | Hayden et al. ............. 502/218 |
| 5,100,859 A | 3/1992 | Gerdes et al. .............. 502/439 |
| 5,102,848 A | 4/1992 | Soo et al. ................... 502/218 |
| 5,145,824 A | 9/1992 | Buffum et al. ............. 502/216 |
| 5,155,242 A | 10/1992 | Shankar et al. ............ 549/534 |
| 5,187,140 A | 2/1993 | Thorsteinson et al. ...... 502/348 |
| 5,262,551 A | 11/1993 | Horrell, Jr. et al. ........ 549/534 |
| 5,364,826 A | 11/1994 | Kemp ......................... 502/315 |
| 5,380,697 A | 1/1995 | Matusz et al. .............. 502/348 |
| 5,380,885 A | 1/1995 | Kemp ......................... 549/536 |
| 5,387,751 A | 2/1995 | Hayden et al. ............. 549/534 |
| 5,418,202 A | 5/1995 | Evans et al. ................ 502/348 |
| 5,447,897 A | 9/1995 | Kemp ......................... 502/303 |
| 5,486,628 A | 1/1996 | Kemp ......................... 549/536 |
| 5,504,052 A | 4/1996 | Rizkalla et al. ............ 502/347 |
| 5,504,053 A | 4/1996 | Chou et al. ................. 502/348 |
| 5,545,603 A | 8/1996 | Kemp ......................... 502/347 |
| 5,597,773 A | 1/1997 | Evans et al. ................ 502/348 |
| 5,663,385 A | 9/1997 | Kemp ......................... 549/536 |
| 5,703,253 A | 12/1997 | Evans et al. ................ 549/536 |
| 5,739,075 A | 4/1998 | Matusz ....................... 502/302 |
| 5,770,746 A | 6/1998 | Cooker et al. .............. 549/534 |
| 5,801,259 A | 9/1998 | Kowaleski .................. 549/536 |
| 5,864,047 A | 1/1999 | Gaffney ...................... 549/536 |
| 6,011,163 A | 1/2000 | Barnicki et al. ............ 549/534 |
| 6,368,998 B1 | 4/2002 | Lockemeyer ............... 502/347 |
| 6,372,925 B1 | 4/2002 | Evans et al. ................ 549/536 |
| 6,717,001 B2 | 4/2004 | Evans et al. ................ 549/536 |

FOREIGN PATENT DOCUMENTS

| | | | |
|---|---|---|---|
| AU | 18818/70 | 2/1927 | |
| BE | 707567 | 5/1968 | |
| CA | 488990 | 12/1952 | .............. 260/372.7 |
| CA | 1286687 | 7/1991 | |
| EP | 003642 A2 | 8/1979 | |
| EP | 0057066 | 8/1982 | |
| EP | 0176253 | 8/1985 | |

(Continued)

OTHER PUBLICATIONS

Kirk-Othmer's Encyclopedia Of Chem. Tech., $3^{rd}$ Ed., vol. 9 (1980), pp. 445-447.

Brunauer, S., Emmett, P. Y. and Teller, E., J. Am. Chem. Soc., 60, 309-16 (1938).

Serafin, J.G. et al., Surface Science and the Silver-catalyzed Epoxidation of Ethylene: An Industrial Perspective, Journal of Molecular Catalysis A: Chemical 131 (1998) pp. 157-168, XP-002230219.

Reiss, Luft, Chenue Ingenieur Technik (1997), 69(ii), 1638-1641. (English translation provided).

"Chlorierte Kohlenwasserstoffe als Inhibitoren in der Ethylenoxid-Synthese Teil 1: Vergleich der Wirksamkeit," by Thomas Reiss and Gerhard Luft, Chem.-Ing.-Tech. 67 (1995), p. 208. (English translation provided).

(Continued)

*Primary Examiner*—Bernard Dentz

(57) ABSTRACT

A reaction system for epoxidation of olefins, with a feed control system configured to control the relative quantity of reaction modifier present in the feed, where the relative quantity of said reaction modifier is changed in response to changes in the reaction temperature.

16 Claims, 1 Drawing Sheet

FOREIGN PATENT DOCUMENTS

| | | |
|---|---|---|
| EP | 0266852 | 11/1987 |
| EP | 266015 A1 | 5/1988 |
| EP | 0299569 | 7/1988 |
| EP | 0352849 | 7/1989 |
| EP | 0357292 | 8/1989 |
| EP | 352850 A1 | 1/1990 |
| EP | 0425020 | 10/1990 |
| EP | 0480538 | 10/1991 |
| EP | 0496470 | 1/1992 |
| EP | 0567273 | 10/1993 |
| EP | 0393785 | 1/1995 |
| EP | 1458698 | 9/2004 |
| EP | 1458699 | 9/2004 |
| GB | 1055147 | 1/1967 |
| GB | 1213483 | 11/1970 |
| GB | 1314613 | 4/1973 |
| JP | 2002248351 | 9/2002 |
| WO | WO 95/17957 | 7/1995 |
| WO | WO97/10232 | 3/1997 |
| WO | WO9713579 | 4/1997 |
| WO | WO97/28142 | 8/1997 |
| WO | WO 98/58920 | 12/1998 |
| WO | WO 00/15333 | 3/2000 |
| WO | WO 00/15334 | 3/2000 |
| WO | WO 00/15335 | 3/2000 |
| WO | WO 01/96324 A2 | 12/2001 |
| WO | WO 01/96324 A3 | 12/2001 |

OTHER PUBLICATIONS

"Ethylene Oxide Synthesis," by J. M. Berty, *Applied Industrial Catalysis*, vol. 1, 1983, pp. 207-239.

*Advanced Inorganic Chemistry A Comprehensive Text*, F. Albert Cotton and Geoffrey Wilkinson, F.R.S., Interscience Publishers, A Division of John Wiley & Sons, New York, London, Sydney (1966) p. 335.

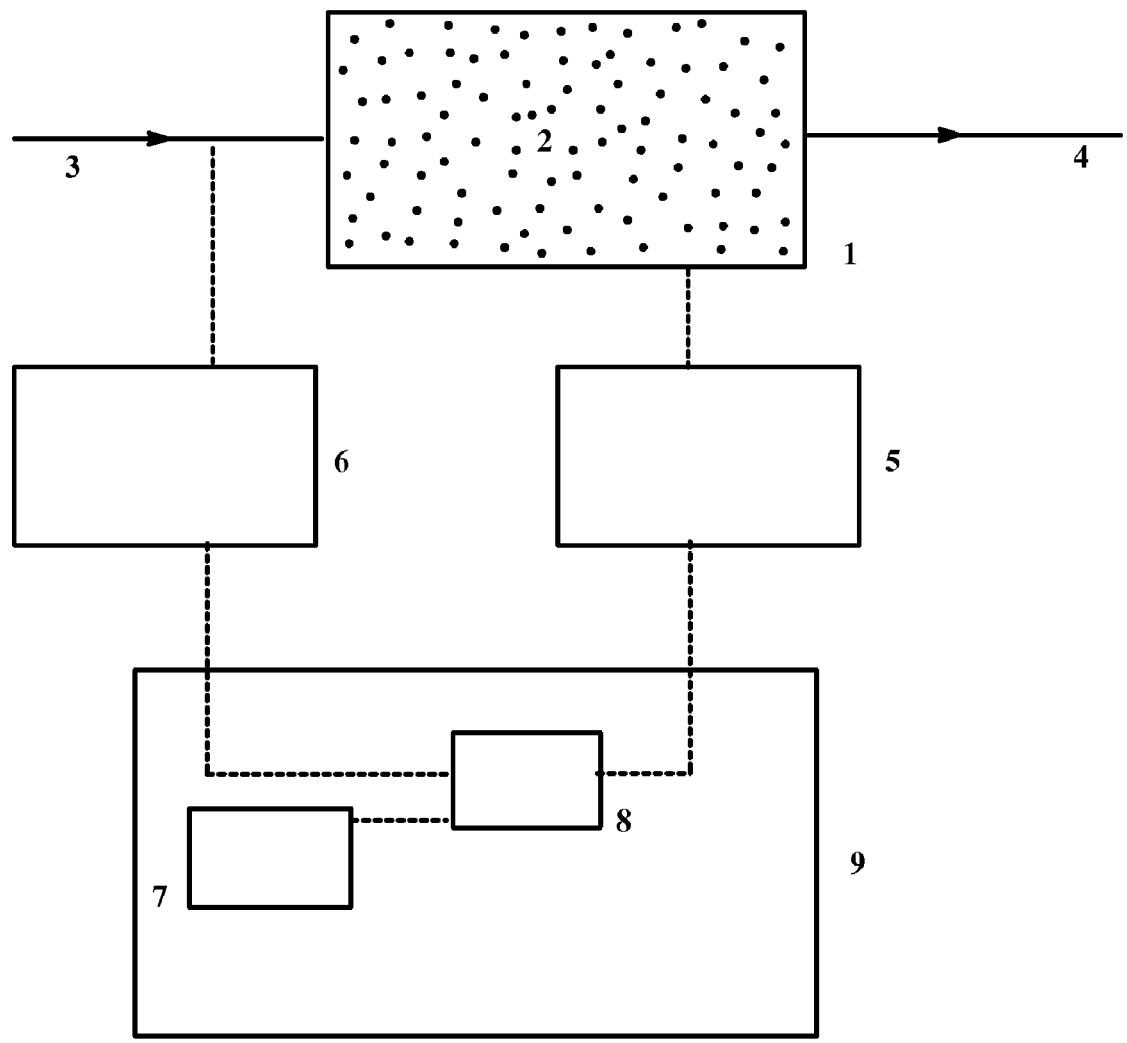
FIGURE

PROCESS AND SYSTEMS FOR THE EPOXIDATION OF AN OLEFIN

CROSS-REFERENCE TO RELATED APPLICATIONS

This application is a divisional of U.S. patent application Ser. No. 10/404,829, filed Apr. 1, 2003 now U.S. Pat. No. 7,193,094, the entire disclosure of which is hereby incorporated by reference, which is a continuation in part of U.S. application Ser. No. 10/299,878, filed Nov. 19, 2002, now abandoned, the entire disclosure of which is hereby incorporated by reference, which claims the benefit of U.S. Provisional Application Ser. No. 60/331,828, filed Nov. 20, 2001, now abandoned, the entire disclosure of which is hereby incorporated by reference.

FIELD OF THE INVENTION

The invention relates to a process for the epoxidation of an olefin, which process comprises reacting a feed comprising the olefin, oxygen and a reaction modifier in the presence of a highly selective silver-based catalyst. The invention also relates to systems suitable for use in connection with the process.

BACKGROUND OF THE INVENTION

The catalytic epoxidation of olefins using a silver-based catalyst has been known for a long time. Conventional silver-based catalysts have provided the olefin oxides notoriously in a low selectivity. For example, when using conventional catalysts in the epoxidation of ethylene, the selectivity towards ethylene oxide, expressed as a fraction of the ethylene converted, does not reach values above the 6/7 or 85.7 mole-% limit. Therefore, this limit has long been considered to be the theoretically maximal selectivity of this reaction, based on the stoichiometry of the reaction equation $$7C_2H_4 + 6O_2 => 6C_2H_4O + 2CO_2 + 2H_2O,$$

cf. Kirk-Othmer's *Encyclopedia of Chemical Technology*, $3^{rd}$ ed., Vol. 9, 1980, p. 445.

Modern silver-based catalysts however are highly selective towards olefin oxide production. When using the modern catalysts in the epoxidation of ethylene the selectivity towards ethylene oxide can reach values above the 6/7 or 85.7 mole-% limit referred to, for example 88 mole-%, or 89 mole-%, or above. Such highly selective catalysts, which may comprise as their active components silver, rhenium, at least one further metal and optionally a rhenium co-promoter, are disclosed in U.S. Pat. No. 4,761,394, U.S. Pat. No. 4,766,105, EP-A-266015 and in several subsequent patent publications.

The silver based catalysts are subject to an aging-related performance decline during normal operation and they need to be exchanged periodically. The aging manifests itself by a reduction in the activity of the catalyst. Usually, when a reduction in activity of the catalyst is manifest, the reaction temperature is increased in order to compensate for the reduction in activity. The reaction temperature may be increased until it becomes undesirably high, at which point in time the catalyst is deemed to be at the end of its lifetime and would need to be exchanged.

A reaction modifier, for example an organic halide, may be added to the feed to an epoxidation reactor for increasing the selectivity (cf. for example EP-A-352850). The reaction modifier suppresses the undesirable oxidation of olefin or olefin oxide to carbon dioxide and water, relative to the desired formation of olefin oxide, by a so-far unexplained mechanism.

The optimal quantity of the reaction modifier depends on the epoxidation reaction conditions and on the type of catalyst used. Conventional catalysts have relatively flat selectivity curves for the modifier, i.e. the curves of the selectivity as a function of the quantity of the reaction modifier show that the selectivities are almost invariant over a wide range of reaction modifier quantities, and this property does virtually not change as a function of the reaction temperature and during prolonged operation of the catalyst. Therefore, when using a conventional catalyst, for optimum selectivity the quantity of the reaction modifier can be chosen rather freely and it can remain substantially the same during the entire lifetime of the catalyst.

By contrast, the highly selective catalysts tend to exhibit relatively steep selectivity curves for the modifier, viz. for the highly selective catalysts the selectivity varies considerably with relatively small changes in the quantity of the reaction modifier, and the selectivity exhibits a pronounced maximum, i.e. an optimum, at a certain quantity of the reaction modifier. This has been illustrated in EP-A-352850 (cf. FIG. 3 therein). Moreover, the selectivity curves and more in particular this quantity of the reaction modifier where the selectivity is at optimum tend to change with the reaction temperature and, thus, during the catalyst life.

Consequently, when employing the highly selective catalysts in combination with a reaction modifier, the selectivity may vary to an undesirably large extent with changes of the reaction temperature and over the lifetime of the catalyst. Namely, when the reaction temperature is changed, for example to compensate for a reduction in the activity of the catalyst, it represents itself as a problem to maintain reaction conditions which are optimal with respect to the selectivity towards the olefin oxide production.

SUMMARY OF THE INVENTION

More of the reaction modifier will generally be needed to achieve a certain effect as the concentration of hydrocarbons in the feed changes to a higher value, and vice versa. It is thought that, unlike other components of the feed, the hydrocarbons present (for example, the olefin and saturated hydrocarbons, if present) have an ability to remove or strip reaction modifier from the catalyst and it is the concentration of the modifier's active species on the catalyst which needs to be maintained, as opposed to the concentration of the reaction modifier in the reaction mixture at places other than the catalyst surface. For this reason, the relative quantity Q of the reaction modifier is considered. The relative quantity Q is basically the ratio of the molar quantity of the reaction modifier to the molar quantity of hydrocarbons as present in the feed. However, as there may be differences in the removing/stripping behavior of the various hydrocarbons in the feed, it may be preferred, when calculating Q, to replace the molar quantity of hydrocarbons by a-so-called-effective molar quantity of hydrocarbons. The effective molar quantity of hydrocarbons in the feed can be calculated from the feed composition (as set out hereinafter), such that it accounts for the differences in the removing/stripping behavior between the hydrocarbons present. There may also be differences in the behavior of different reaction modifiers, while in practice a mixture of reaction modifiers is frequently present. Therefore it may be preferred, when calculating Q, also to replace the molar quantity of the reaction modifier by a-so-called-effective molar quantity of active species of the reaction modifier. The effective molar quantity of active species of the reaction modifier in the feed can be calculated from the feed composition (as set out hereinafter), such that it accounts for the differences in the behavior of different reaction modifiers.

For the highly selective catalysts it has surprisingly been found that when the reaction temperature is increased or decreased the position of the selectivity curve for the modifier shifts towards a higher value of Q or a lower value of Q, respectively, proportionally with the change in the reaction temperature. The proportionality of this shift is independent of the degree of aging of the catalyst and can be determined and verified by routine experimentation.

As a consequence of this finding, when the reaction temperature is changed in the course of the epoxidation process undesirable deviations from the optimum selectivity can be reduced or prevented by adjusting the value of Q proportionally to the change in the reaction temperature. This is particularly useful when the process is operated at optimum conditions with respect to the selectivity, in which case optimum conditions can be maintained by changing the value of Q in proportion to a change in reaction temperature. This all is even more useful when an increase in reaction temperature is employed in response to a reduction in the activity of the catalyst. The invention enables predetermining, for example by calculation, an appropriate change in the value of Q, and therefore in the composition of the reaction modifier and/or the hydrocarbons, in response to a change in the reaction temperature. It is an advantage of this invention that concurrently with the change in reaction temperature there may be changes in the feed composition other than those relating to the hydrocarbons and/or the reaction modifier. Thus, it is a benefit of the present invention that it allows the epoxidation process to be controlled significantly more simply and more smoothly than without the invention.

Accordingly, the present invention provides a process for the epoxidation of an olefin, which process comprises reacting a feed comprising the olefin, oxygen and a reaction modifier in the presence of a highly selective silver-based catalyst at a reaction temperature T, and with the reaction modifier being present in a relative quantity Q which is the ratio of an effective molar quantity of active species of the reaction modifier present in the feed to an effective molar quantity of hydrocarbons present in the feed, and which process comprises the steps of:

operating at a first operating phase wherein the value of T is $T_1$ and the value of Q is $Q_1$, and subsequently operating at a second operating phase at a reaction temperature which is different from the reaction temperature employed in the first operating phase, such that the value of T is $T_2$ and the value of Q is substantially $Q_2$, whereby $Q_2$ is determined by calculation and $Q_2$ is defined by the formula $$Q_2 = Q_1 + B(T_2 - T_1),$$

wherein B denotes a constant factor which is greater than 0.

The invention also provides a reaction system suitable for performing a process for the epoxidation of an olefin, which reaction system comprises a reactor holding a highly selective silver-based catalyst, being configured to receive a feed comprising the olefin, oxygen and a reaction modifier and having a temperature control system configured to control in the reactor a reaction temperature T, which reaction system further comprises a feed control system configured to control the reaction modifier being present in the feed in a relative quantity Q which is the ratio of an effective molar quantity of active species of the reaction modifier present in the feed to an effective molar quantity of hydrocarbons present in the feed, and which reaction system is configured to perform the process steps of:

operating at a first operating phase wherein the value of T is $T_1$ and the value of Q is $Q_1$, and subsequently operating at a second operating phase at a reaction temperature which is different from the reaction temperature employed in the first operating phase, such that the value of T is $T_2$ and the value of Q is substantially $Q_2$, whereby $Q_2$ can be determined by calculation and $Q_2$ is defined by the formula $$Q_2 = Q_1 + B(T_2 - T_1),$$

wherein B denotes a constant factor which is greater than 0.

The invention enables to optimally retain the benefits of the reaction modifier while changing the reaction temperature, by maintaining the concentration of the modifier's active species on the catalyst, as opposed to maintaining the concentration of the reaction modifier in the reaction mixture at places other than the catalyst surface. Maintaining the concentration of the modifier's active species on the catalyst is (substantially) achieved when the process is operated in accordance with the formula as defined, in response to a change in reaction temperature. The skilled person is well aware that the formula as defined may be replaced by another mathematical expression, for example a polynomial or exponential expression, which may be constructed such that it provides essentially the same result within the relevant numerical ranges of the variables involved, in particular the ranges as defined hereinafter for values of Q ($Q_1$ and/or $Q_2$) and the reaction temperature T ($T_1$, $T_2$ and/or $T_2 - T_1$). Such embodiments, i.e. which use such an equivalent mathematical expression, fall within the scope of the present invention.

The invention also provides a computer program product which comprises a computer readable medium and a computer readable program code, recorded on the computer readable medium, suitable for instructing a data processing system of a computer system to execute calculations for a process for the epoxidation of an olefin, which process comprises reacting a feed comprising the olefin, oxygen and a reaction modifier in the presence of a highly selective silver-based catalyst at a reaction temperature T, and with the reaction modifier being present in a relative quantity Q which is the ratio of an effective molar quantity of active species of the reaction modifier present in the feed to an effective molar quantity of hydrocarbons present in the feed, and which process comprises the steps of:

operating at a first operating phase wherein the value of T is $T_1$ and the value of Q is $Q_1$, and subsequently operating at a second operating phase at a reaction temperature which is different from the reaction temperature employed in the first operating phase, such that the value of T is $T_2$ and the value of Q is substantially $Q_2$ which is calculated by using the formula $$Q_2 = Q_1 + B(T_2 - T_1),$$

wherein B denotes a constant factor which is greater than 0, or by using another mathematical expression which is constructed such that it provides essentially the same result as the formula.

The invention also provides a computer system which comprises a computer program product and a data processing system configured to receive instructions read from the computer program product, wherein the computer program product comprises a computer readable medium and a computer readable program code, recorded on the computer readable medium, suitable for instructing the data processing system to execute calculations for a process for the epoxidation of an olefin, which process comprises reacting a feed comprising the olefin, oxygen and a reaction modifier in the presence of a highly selective silver-based catalyst at a reaction temperature T, and with the reaction modifier being present in a relative quantity Q which is the ratio of an effective molar quantity of active species of the reaction modifier present in the feed to an effective molar quantity of hydrocarbons present in the feed, and which process comprises the steps of:

operating at a first operating phase wherein the value of T is $T_1$ and the value of Q is $Q_1$, and subsequently operating at a second operating phase at a reaction temperature which is different from the reaction temperature employed in the first operating phase, such that the value of T is $T_2$ and the value of Q is substantially $Q_2$ which is calculated by using the formula $$Q_2 = Q_1 + B(T_2 - T_1),$$

wherein B denotes a constant factor which is greater than 0, or by using another mathematical expression which is constructed such that it provides essentially the same result as the formula.

The present invention also provides, in more general terms, a process for the epoxidation of an olefin, which process comprises reacting a feed comprising the olefin, oxygen and a reaction modifier in the presence of a highly selective silver-based catalyst, and which process comprises the steps of:

operating at a first operating phase, and subsequently operating at a second operating phase at a reaction temperature which is different from the reaction temperature employed in the first operating phase, such that the concentration of active species of the reaction modifier on the catalyst is substantially unchanged.

BRIEF DESCRIPTION OF THE FIGURE

The FIGURE shows a schematic representation of the reaction system of this invention in association with the computer system of this invention and the computer program product of this invention

DETAILED DESCRIPTION OF THE INVENTION

Although the present epoxidation process may be carried out in many ways, it is preferred to carry it out as a gas phase process, i.e. a process in which the feed is contacted in the gas phase with the catalyst which is present as a solid material, typically in a packed bed. Generally the process is carried out as a continuous process. Frequently, in commercial scale operation, the process of the invention may involve a quantity of catalyst which is at least 10 kg, for example at least 20 kg, frequently in the range of from $10^2$ to $10^7$ kg, more frequently in the range of from $10^3$ to $10^6$ kg.

The olefin for use in the present epoxidation process may be any olefin, such as an aromatic olefin, for example styrene, or a di-olefin, whether conjugated or not, for example 1,9-decadiene or 1,3-butadiene. Typically, the olefin is a monoolefin, for example 2-butene or isobutene. Preferably, the olefin is a mono-α-olefin, for example 1-butene or propylene. The most preferred olefin is ethylene.

The olefin concentration in the feed is not material to this invention and may be selected within a wide range. Typically, the olefin concentration in the feed will be at most 80 mole-%, relative to the total feed. Preferably, it will be in the range of from 0.5 to 70 mole-%, in particular from 1 to 60 mole-%, on the same basis. As used herein, the feed is considered to be the composition which is contacted with the catalyst. If desired, the olefin concentration may be increased during the lifetime of the catalyst, by which the selectivity may be improved in an operating phase wherein the catalyst has aged (cf. U.S. Pat. No. 6,372,925-B1 and WO-A-01/96324, i.e. non-prepublished PCT patent application PCT/US01/18097).

The present epoxidation process may be air-based or oxygen-based, see Kirk-Othmer's *Encyclopedia of Chemical Technology*, 3rd ed., Vol. 9, 1980, p. 445-447. In the air-based process air or air enriched with oxygen is employed as the source of the oxidizing agent while in the oxygen-based processes high-purity (>95 mole-%) oxygen is employed as the source of the oxidizing agent. Presently most epoxidation plants are oxygen-based and this is a preferred embodiment of the present invention.

The oxygen concentration in the feed is not material to this invention and may be selected within a wide range. However, in practice, oxygen is generally applied at a concentration which avoids the flammable regime. Typically, the concentration of oxygen applied will be within the range of from 1 to 15 mole-%, more typically from 2 to 12 mole-% of the total feed.

In order to remain outside the flammable regime, the concentration of oxygen in the feed may be lowered as the concentration of the olefin is increased. The actual safe operating ranges depend, along with the feed composition, also on the reaction conditions such as the reaction temperature and the pressure.

The reaction modifier is present in the feed for increasing the selectivity, suppressing the undesirable oxidation of olefin or olefin oxide to carbon dioxide and water, relative to the desired formation of olefin oxide. Many organic compounds, especially organic halides and organic nitrogen compounds, may be employed as the reaction modifier. Nitrogen oxides, hydrazine, hydroxylamine or ammonia may be employed as well. It is frequently considered that under the operating conditions of olefin epoxidation the nitrogen containing reaction modifiers are precursors of nitrates or nitrites, i.e. they are so-called nitrate- or nitrite-forming compounds (cf. e.g. EP-A-3642, U.S. Pat. No. 4,822,900).

Organic halides are the preferred reaction modifiers, in particular organic bromides, and more in particular organic chlorides. Preferred organic halides are chlorohydrocarbons or bromohydrocarbons. More preferably they are selected from the group of methyl chloride, ethyl chloride, ethylene dichloride, ethylene dibromide, vinyl chloride or a mixture thereof. Most preferred reaction modifiers are ethyl chloride and ethylene dichloride.

Suitable nitrogen oxides are of the general formula $NO_x$ wherein x, which denotes the ratio of the number of oxygen atoms to the number of nitrogen atoms, is in the range of from 1 to 2. These nitrogen oxides include for example NO, $N_2O_3$ and $N_2O_4$. Suitable organic nitrogen compounds are nitro compounds, nitroso compounds, amines, nitrates and nitrites, for example nitromethane, 1-nitropropane or 2-nitropropane. In preferred embodiments, nitrate- or nitrite-forming compounds, e.g. nitrogen oxides and/or organic nitrogen compounds, are used together with an organic halide, in particular an organic chloride.

Although the reaction modifier may be supplied as a single compound, upon contact with the catalyst a variety of compounds may be formed which function as reaction modifier, and which may be present in the feed if a recycle is applied. For example, when applying ethyl chloride in an ethylene oxide process, the feed may in practice comprise ethyl chloride, vinyl chloride, ethylene dichloride and methyl chloride.

The reaction modifiers are generally effective when used in low concentration in the feed, for example up to 0.1 mole-%, relative to the total feed, for example from $0.01 \times 10^{-4}$ to 0.01 mole-%. In particular when the olefin is ethylene, it is preferred that the reaction modifier is present in the feed at a concentration of from $0.05 \times 10^{-4}$ to $50 \times 10^{-4}$ mole-%, in particular from $0.2 \times 10^{-4}$ to $30 \times 10^{-4}$ mole-%, relative to the total feed.

In addition to the olefin, oxygen and the reaction modifier, the feed may contain one or more optional components, such as carbon dioxide, water, inert gases and saturated hydrocarbons. Carbon dioxide and water are a by-products of the epoxidation process. Carbon dioxide generally has an adverse effect on the catalyst activity. Typically, a concentration of carbon dioxide in the feed in excess of 10 mole-%, preferably in excess of 5 mole-%, relative to the total feed, is avoided. A concentration of carbon dioxide as low as 1 mole-% or lower, relative to the total feed, may be employed. Water may be introduced in the feed as a result of the recovery of olefin oxide and carbon dioxide from the reaction product. Water generally has an adverse effect on the catalyst activity. Typically, a concentration of water in the feed in excess of 3 mole-%, preferably in excess of 1 mole-%, relative to the total feed, is avoided. A concentration of water as low as 0.2 mole-% or lower, relative to the total feed, may be employed. Inert gas, for example nitrogen or argon, or a mixture thereof, may be present in the feed in a concentration of from 0.5 to 95 mole-%. In an air based process inert gas may be present in the feed in a concentration of from 30 to 90 mole-%, typically from 40 to 80 mole-%. In an oxygen based process inert gas may be present in the feed in a concentration of from 0.5 to 30 mole-%, typically from 1 to 15 mole-%. Suitable saturated hydrocarbons are propane and cyclopropane, and in particular methane and ethane. If saturated hydrocarbons are present, they may be present in a quantity of up to 80 mole-%, relative to the total feed, in particular up to 75 mole-%. Frequently they are present in a quantity of at least 30 mole-%, more frequently at least 40 mole-%. Saturated hydrocarbons may be added to the feed in order to increase the oxygen flammability limit.

The relative quantity Q of the reaction modifier is the ratio of the effective molar quantity of active species of the reaction modifier present in the feed to the effective molar quantity of hydrocarbons present in the feed, both molar quantities being expressed in the same units, for example as mole-%, based on the total feed.

When the reaction modifier is a halogen compound, for the purpose of calculating the effective molar quantity of active species of the reaction modifier and the value of Q, the number of active species is deemed to be the number of halogen atoms, and when the reaction modifier is a nitrate- of nitrite-forming compound, the number of active species is deemed to be the number of nitrogen atoms. This implies, for example, that 1 mole of ethylene dichloride provides about 2 moles of active species, i.e. all of the chlorine atoms present provide an active species. On the other hand, it has also been found that reaction modifiers which are methyl compounds, such as methyl chloride and methyl bromide, are less responsive and therefore from 2 to 5 moles, in particular from 2.5 to 3.5 moles, suitably about 3 moles of the methyl compounds may be deemed to provide 1 mole of the active species. This number may be determined and verified by routine experimentation, and—without wishing to be bound by theory—it is believed that this number is higher as the methyl compound in question has a lesser ability to split off the heteroatom in question (for example the halogen or nitrogen atom). Thus, for example, when the feed comprises $2 \times 10^{-4}$ mole-% of ethyl chloride, $3 \times 10^{-4}$ mole-% of vinyl chloride, $1 \times 10^{-4}$ mole-% of ethylene dichloride and $1.5 \times 10^{-4}$ mole-% of methyl chloride, the effective molar quantity of active species of the reaction modifier may be calculated to amount to $$(2 \times 10^{-4} \times 1) + (3 \times 10^{-4} \times 1) + (1 \times 10^{-4} \times 2) + (1.5 \times 10^{-4} \times \frac{1}{3}) = 7.5 \times 10^{-4} \text{ mole-\%}.$$

Summarizing, the effective molar quantity of active species of the reaction modifier present in the feed may be calculated by multiplying the molar quantity of each of the reaction modifiers present in the feed with a factor, and adding up the multiplication products, wherein each factor represents the number of active heteroatoms, in particular halogen atoms and/or nitrogen atoms, present per molecule of the reaction modifier in question, on the understanding that the factor for a reaction modifier which is a methyl compound may be in the range of from $\frac{1}{5}$ to $\frac{1}{2}$, more typically from $\frac{1}{3.5}$ to $\frac{1}{2.5}$, suitably about $\frac{1}{3}$.

The hydrocarbons present in the feed comprise the olefin and any saturated hydrocarbon present. As indicated hereinbefore, it is thought that the hydrocarbons present in the feed have the ability to remove/strip reaction modifier from the catalyst surface and the extent to which they have this ability may differ for the various hydrocarbons. In order to account for these differences (relative to ethylene), the molar quantity of each of the hydrocarbons present is multiplied with a factor, before the molar quantities are added up to calculate the effective molar quantity of the hydrocarbons. Herein, the factor of ethylene is 1, by definition; the factor for methane may be at most 0.5, or at most 0.4, typically in the range of from 0 to 0.2, more typically in the range of from 0 to 0.1; the factor for ethane may be in the range of from 50 to 150, more typically from 70 to 120; and the factor for higher hydrocarbons (i.e. having at least 3 carbon atoms) may be in the range of from 10 to 10000, more typically from 50 to 2000. Such factors may be determined and verified by routine experimentation, and—without wishing to be bound by theory—it is believed that the factor is higher as the hydrocarbon in question has a greater ability to form radicals. Suitable factors for methane, ethane, propane and cyclopropane, relative to ethylene, are about 0.1, about 85, about 1000 and about 60, respectively. As an example, when the feed comprises 30 mole-% ethylene, 40 mole-% of methane, 0.4 mole-% of ethane and 0.0001 mole-% of propane, the effective molar quantity of the hydrocarbons may be calculated to amount to $$(30 \times 1) + (40 \times 0.1) + (0.4 \times 85) + (0.0001 \times 1000) = 68.1 \text{ mole-\%}.$$

It is noted that when ethylene oxide is produced from ethylene without further hydrocarbons being present, the effective molar quantity of the hydrocarbons equals the actual molar quantity, and that the addition of ethane or higher hydrocarbons to an ethylene feed contributes significantly to the effective molar quantity, whereas there is relatively little contribution from any methane added.

Eligible values of Q are at least $1 \times 10^{-6}$, and in particular at least $2 \times 10^{-6}$. Eligible values of Q are at most $100 \times 10^{-6}$, and in particular at most $50 \times 10^{-6}$.

In any operating phase of the process the value of Q may be adjusted so as to achieve an optimal selectivity towards the olefin oxide formation. In practice, the value of Q may be adjusted by adjusting the quantity of the reaction modifier present in the feed, while not changing the hydrocarbon concentrations in the feed.

The present epoxidation process may be carried out using reaction temperatures selected from a wide range. In Preferred embodiments the reaction temperature T is expressed in ° C., but other temperatures units are also possible, for example ° F. Preferably the reaction temperature T is in the range of from 180 to 340° C., more preferably in the range of from 190 to 325° C., in particular in the range of from 200 to 300° C. The epoxidation process may be carried out such that the reaction temperature is not the same at every catalyst particle. If this is the case, the reaction temperature is deemed to be the weight average temperature of the catalyst particles. On the other hand, when the reaction temperature is not the same at every catalyst particle, still the value of the difference $T_2-T_1$ may practically be the same for all catalyst particles, and may be more easily determined than the separate values of $T_1$ and $T_2$. The difference $T_2-T_1$ may be equal to a corresponding difference in coolant temperature.

In accordance with this invention, when the reaction temperature is changed from $T_1$ to $T_2$, the value of Q may be changed from $Q_1$ to $Q_2$, so that deviations from the optimum selectivity which would result from the change in reaction temperature are reduced or even prevented. The value of $Q_2$ is typically a calculated value, calculated on the basis of $T_1$, $T_2$ and $Q_1$. In particular, $Q_2$ can be calculated by using the formula $$Q_2=Q_1+B(T_2-T_1)$$

(i.e. formula (I)), wherein B denotes a constant factor which is greater than 0. If the reaction temperature T is expressed in ° C., B is expressed in (° C.)$^{-1}$. In this patent document, all numerical values of B are expressed in (° C.)$^{-1}$. The skilled person will be able to convert the numerical values of B expressed in (° C.)$^{-1}$ to values expressed in another unit which is consistent with the unit in which the reaction temperature T is expressed. The value of B is not material to this invention. The value of B may eligibly be at least $0.01 \times 10^{-6}$, in particular at least $0.1 \times 10^{-6}$. The value of B may eligibly be at most $1 \times 10^{-6}$, in particular at most $0.5 \times 10^{-6}$. Without wishing to be bound by theory, it is thought that the value of B may be dependent of the composition of the catalyst, in particular the catalytically active metals present, and the nature of the active species of the reaction modifier. Suitable values of B may be determined and verified by routine experimentation. A suitable value of B amounts to about $0.22 \times 10^{-6}$, in particular when used in combination with the numbers and factors employed in the example calculations of the effective molar quantity of active species of the reaction modifier and the effective molar quantity of the hydrocarbons, as given hereinbefore.

As used herein, the expression "the value of Q is substantially $Q_2$" will be understood by the skilled person as relating, for example, to abilities in process control. By the expression it may be meant that, for example, the value of Q is within a range of from 0.6 to 1.4 times the value of $Q_2$, more typically within a range of from 0.7 to 1.3 times the value of $Q_2$, most typically within a range of from 0.8 to 1.2 times the value of $Q_2$.

It is preferred to operate the epoxidation process at the reaction temperature $T_1$ employing such a value of $Q_1$ that the selectivity towards the olefin oxide formation is optimal. When this is the case, the epoxidation process will continue to operate at an optimum selectivity, but not necessarily the same selectivity, when employing the reaction temperature $T_2$ and the value of $Q_2$ in accordance with formula (I).

The reaction temperature may be changed for many purposes. For example, the reaction temperature may be decreased to slow down the epoxidation reaction when the need thereto arises. Alternatively, the reaction temperature may be increased, to speed up the epoxidation reaction, so that more of the olefin oxide is produced per time unit. Combinations are conceivable, for example a temperature increase may after a period of time be followed by a temperature decrease, and vice versa. Any change in the reaction temperature may be gradual, or step wise, for example in one or more steps of 0.1 to 20° C., in particular 0.2 to 10° C., more in particular 0.5 to 5° C., and any change in the reaction temperature may be accompanied with a change in the value of Q in accordance with this invention. Generally, the change in the value of Q from $Q_1$ to $Q_2$ is made co-currently with the change from $T_1$ to $T_2$.

Preferably, as the catalyst ages, the reaction temperature is changed as to compensate for a reduction in the activity of the catalyst. The activity of the catalyst may be monitored by the production rate of the olefin oxide. In order to compensate for the reduction in the activity of the catalyst, the reaction temperature may be increased gradually or in a plurality of steps, for example in steps of from 0.1 to 20° C., in particular 0.2 to 10° C., more in particular 0.5 to 5° C., with co-current changes in the value of Q, in accordance with formula (I).

In particular in a process for preparing ethylene oxide from ethylene, when a fresh catalyst is used, the reaction temperature is typically in the range of from 180 to 300° C., more typically from 180 to 280° C., in particular in the range of from 190 to 270° C., more in particular from 200 to 260° C.; the value of Q is typically in the range of from $1 \times 10^{-6}$ to $20 \times 10^{-6}$, more typically from $3 \times 10^{-6}$ to $15 \times 10^{-6}$; and the concentration of the reaction modifier in the feed is typically in the range of from $0.2 \times 10^{-4}$ to $10 \times 10^{-4}$ mole-%, preferably from $1 \times 10^{-4}$ to $8 \times 10^{-4}$ mole-%, relative to the total feed. In order to compensate for the reduction in the activity of the catalyst, the reaction temperature may be increased gradually or in a plurality of steps typically to a level in the range of from 230 to 340° C., more typically from 240 to 325° C., in particular from 250 to 300° C. The total increase in the reaction temperature may be in the range of from 10 to 140° C., more typically from 20 to 100° C. Typically, the value of Q employed after accomplishing such an increase in reaction temperature may be in the range of from $5 \times 10^{-6}$ to $100 \times 10^{-6}$, more typically from $10 \times 10^{-6}$ to $50 \times 10^{-6}$; and the concentration of the reaction modifier in the feed is increased typically to values in the range of from $1 \times 10^{-4}$ to $40 \times 10^{-4}$ mole-%, preferably from $1.5 \times 10^{-4}$ to $30 \times 10^{-4}$ mole-%, relative to the total feed. Herein, a "fresh catalyst" means a catalyst which, in the course of operation of the epoxidation process, has not reached an age defined by a cumulative olefin oxide production of at least $2 \times 10^6$ mole olefin oxide per m$^3$ of catalyst.

It is an advantage of this invention that any change in the value of Q may be effected by a change in the concentration or composition of the reaction modifier in the feed, or by a change in the concentration or composition of the hydrocarbons in the feed, or a combination of both. Co-currently with these changes there may or may not be changes in the composition of the feed with respect to other components, such as oxygen, carbon dioxide or inert gases.

Generally, the highly selective silver based catalyst is a supported catalyst. The support may be selected from a wide range of inert support materials. Such support materials may be natural or artificial inorganic materials and they include silicon carbide, clays, pumice, zeolites, charcoal and alkaline earth metal carbonates, such as calcium carbonate. Preferred are refractory support materials, such as alumina, magnesia, zirconia and silica. The most preferred support material is α-alumina.

The support material is preferably porous and has preferably a surface area, as measured by the B.E.T. method, of less than 20 m$^2$/g and in particular from 0.05 to 20 m$^2$/g. More preferably the B.E.T. surface area of the support is in the range of 0.1 to 10, in particular from 0.1 to 3.0 m²/g. As used herein, the B.E.T. surface area is deemed to have been measured by the method as described in Brunauer, Emmet and Teller in *J. Am. Chem. Soc.* 60 (1938) 309-316.

As used herein, a highly selective silver-based catalyst is one which, when operated fresh, can exhibit in the gas phase epoxidation of ethylene a theoretical selectivity at zero oxygen conversion, $S_0$, of at least 6/7 or 85.7%, preferably 88%, more preferably at least 89%. More in particular, this theoretical selectivity can be accomplished at a reaction temperature of 260° C. The value of $S_0$ for a given catalyst is found by operating the catalyst, in particular at a reaction temperature of 260° C., in a range of gas hourly space velocities, resulting in a range of selectivity values and oxygen conversion values corresponding to the range of gas hourly space velocities employed. The selectivity values found are then extrapolated back to the theoretical selectivity at zero oxygen conversion, $S_0$.

Preferred highly selective silver-based catalysts comprise, in addition to silver, one or more of rhenium, molybdenum, tungsten, a Group IA metal, and a nitrate- or nitrite-forming compound, which may each be present in a quantity of from 0.01 to 500 mmole/kg, calculated as the element (rhenium, molybdenum, tungsten, Group IA metal or nitrogen) on the total catalyst. The nitrate- or nitrite-forming compounds and particular selections of nitrate- or nitrite-forming compound are as defined hereinbefore. Rhenium, molybdenum, tungsten, or the nitrate- or nitrite-forming compound may suitably be provided as an oxyanion, for example, as a perrhenate, molybdate, tungstate or nitrate, in salt or acid form.

Of special preference are the silver-based catalysts which comprise rhenium, in addition to silver. Such catalysts are known from U.S. Pat. No. 4,761,394, U.S. Pat. No. 4,766,105 and EP-A-266015. Broadly, they comprise silver, rhenium or compound thereof, a further metal or compound thereof and optionally a rhenium co-promoter which may be selected from one or more of sulfur, phosphorus, boron, and compounds thereof, on the support material. More specifically the further metal is selected from the group of Group IA metals, Group IIA metals, molybdenum, tungsten, chromium, titanium, hafnium, zirconium, vanadium, thallium, thorium, tantalum, niobium, gallium and germanium and mixtures thereof. Preferably the further metal is selected from the Group IA metals such as lithium, potassium, rubidium and cesium and/or from the Group IIA metals such as calcium and barium. Most preferably it is lithium, potassium and/or cesium. Where possible, rhenium, the further metal or the rhenium co-promoter is provided as an oxyanion, in salt or acid form.

Preferred amounts of the components of these catalysts are, when calculated as the element on the total catalyst:

silver from 10 to 500 g/kg, rhenium from 0.01 to 50 mmole/kg, the further metal or metals from 0.1 to 500 mmole/kg each, and, if present, the rhenium co-promoter or co-promoters from 0.1 to 30 mmole/kg each. More preferably, the rhenium content of these catalysts is above 1.5 mmole/kg and at most 50 mmole/kg, in particular from 1.6 to 40 mmole/kg, when calculated as the element on the total catalyst; alternatively, the rhenium content of these catalysts, expressed relative to the surface area of the support, is preferably above 0.0015 mmole/m², more typically above 0.0016 mmole/m². Preferably the rhenium content is at most 0.1 mmole/m², more preferably at most 0.05 mmole/m², relative to the surface area of the support.

According to this Assignee's co-pending patent application Ser. No. 10/816,080 of even date as the present patent document, the rhenium containing high selectivity catalysts having a low rhenium content have been found to exhibit a behavior similar to the behavior of the conventional catalysts in their response to changes in the concentration of the reaction modifier in the feed. Accordingly, these low rhenium content catalysts are preferably used without increasing the quantity of reaction modifier in the feed when the reaction temperature is increased. The present invention is therefore of less advantage when practiced with catalysts which have a rhenium content of at most 1.5 mmole/kg, calculated as the element on the total catalyst, and at most 0.0015 mmole/m², relative to the surface area of the support, or, more generically, which have their value of $S_0$ in the range of from 85.7 to 88% at a reaction temperature of 260° C.

The present epoxidation process is preferably carried out at a reactor inlet pressure in the range of from 1000 to 4000 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is as a gas phase process involving a packed catalyst bed, the GHSV is in the range of from 1500 to 10000 Nl/(l·h). Preferably, the process of this invention is carried out at a work rate in the range of from 0.5 to 10 kmole olefin oxide produced per m³ of catalyst per hour, in particular 0.7 to 8 kmole olefin oxide produced per m³ of catalyst per hour, for example 5 kmole olefin oxide produced per m³ of catalyst per hour. As used herein, the work rate is the amount of the olefin oxide produced per unit volume of catalyst per hour and the selectivity is the molar quantity of the olefin oxide formed relative to the molar quantity of the olefin converted.

The olefin oxide produced may be recovered from the reaction product by using methods known in the art, for example by absorbing the olefin oxide from a reactor outlet stream in water and optionally recovering the olefin oxide from the aqueous solution by distillation. At least a portion of the aqueous solution containing the olefin oxide may be applied in a subsequent process for converting the olefin oxide into a 1,2-diol or a 1,2-diol ether.

The olefin oxide produced in the present epoxidation process may be converted into a 1,2-diol or into a 1,2-diol ether. As this invention leads to a more attractive process for the production of the olefin oxide, it concurrently leads to a more attractive process which comprises producing the olefin oxide in accordance with the invention and the subsequent use of the obtained olefin oxide in the manufacture of the 1,2-diol and/or 1,2-diol ether.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in presence of an acid catalyst, e.g. 0.5-1.0% w sulfuric acid, based on the total reaction mixture, at 50-70° C. at 1 bar absolute, or in a gas phase reaction at 130-240° C. and 20-40 bar absolute, preferably in the absence of a catalyst. If the proportion of water is lowered the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc.

Unless specified otherwise, the organic compounds mentioned herein, for example the olefins, 1,2-diols, 1,2-diol ethers and reaction modifiers, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

The FIGURE shows the reaction system suitable for performing the process of this invention. The reaction system comprises a reactor (1) holding a highly selective silver-based catalyst (2). The reactor (1) may be configured to receive a feed (3) comprising the olefin, oxygen and the reaction modifier. A reaction product (4) may be produced. The reactor (1) may have a temperature control system (5) configured to control in the reactor (1) the reaction temperature T. The reaction system may further comprise a feed control system (6) configured to control the reaction modifier being present in the feed (3) in the relative quantity Q, and optionally the concentration of other feed components.

The computer program product of this invention (7) may comprise a computer readable medium and a computer readable program code, recorded on the computer readable medium. The computer readable program code may be suitable for instructing a data processing system (8) of the computer system of this invention (9) to execute the calculations in connection with the process of this invention. The computer program product (7) may be in the form of a disk which is a permanent entity of the computer system (9), or it may be a disk which is insertable into the computer system (9). The computer readable medium may be readable, for example, by means of an optical system or by means of a magnetic system.

In a preferred embodiment, the computer program product (7) may comprise, in addition, a computer readable program code, recorded on the computer readable medium, suitable for instructing the data processing system (8) to control the process of this invention. In particular in this preferred embodiment, the computer system may be configured to communicate with the temperature control system (5) and with the feed control system (6). This arrangement of configurations facilitates the control of the process steps of the process of this invention.

The following examples will illustrate the invention.

EXAMPLE 1

A catalyst, as defined in U.S. Pat. No. 4,766,105 (EP-A-266015), containing silver, rhenium, cesium, lithium and tungsten on α-alumina and having a theoretical selectivity $S_0$ of at least 89% at 260° C. in the fresh state was employed in the following experiment.

In the experiment ethylene oxide was produced as follows. A sample of the crushed catalyst (0.8-1.4 mm) was loaded into a micro-reactor consisting of a 3 mm internal diameter stainless steel U-shaped tube. The U-shaped tube was immersed in a molten metal tin/bismuth bath (heat medium) and the ends were connected to a gas flow system. The weight of the catalyst and the inlet gas flow rate were adjusted as to achieve a gas hourly space velocity of 5000 Nl/(l·h). The inlet pressure was 1870 kPa (absolute). The feed to the reactor comprised ethylene at a concentration of 28 mole-%, oxygen at a concentration of 7.4 mole-%, carbon dioxide at a concentration of 5.2 mole-%, ethyl chloride at a concentration of 2.9 ppmv (parts by million by volume), that is such that the selectivity to ethylene oxide is optimal, and the remainder of the feed was nitrogen. The reaction temperature was 257° C., at which temperature the work rate was 208 kg ethylene oxide/(m³·hr). These conditions are hereinafter referred to as "reaction conditions 1".

Subsequently, the reaction conditions 1 were changed to the following: gas hourly space velocity 6000 Nl/(l·h), inlet pressure is 2250 kPa (absolute), ethylene concentration 23 mole-%, oxygen concentration 6.1 mole-%, carbon dioxide concentration of 4.3 mole-%, reaction temperature 263° C. After optimization of the selectivity to ethylene oxide the ethyl chloride concentration was 2.6 ppmv. The work rate was 251 kg ethylene oxide/(m³·hr). These conditions are hereinafter referred to as "reaction conditions 2". By calculation in accordance with formula (I), using B equals $0.22 \times 10^{-6}$ and the reaction conditions 1, it was found that for optimal selectivity to ethylene oxide under the reaction conditions 2 the ethyl chloride concentration should amount to 2.7 ppmv (experimentally found 2.6 ppmv).

Subsequently, the reaction conditions 2 were changed to the following: gas hourly space velocity 7400 Nl/(l·h), inlet pressure is 2650 kPa (absolute), ethylene concentration 19 mole-%, oxygen concentration 5 mole-%, carbon dioxide concentration of 3.5 mole-%, reaction temperature 271° C. After optimization of the selectivity to ethylene oxide the ethyl chloride concentration was 2.6 ppmv. The work rate was 307 kg ethylene oxide/(m³·hr). These conditions are hereinafter referred to as "reaction conditions 3". By calculation in accordance with formula (I), using B equals $0.22 \times 10^{-6}$ and the reaction conditions 1, it was found that for optimal selectivity to ethylene oxide under the reaction conditions 3 the ethyl chloride concentration should amount to 2.6 ppmv (experimentally found 2.6 ppmv).

EXAMPLE 2

A catalyst, as defined in U.S. Pat. No. 4,766,105 (EP-A-266015), containing silver, rhenium, cesium, lithium and sulfur on α-alumina and having a theoretical selectivity $S_0$ of 93% in the fresh state is employed in the following experiment. The above value of $S_0$ was determined by measuring selectivities in a range of gas hourly space velocities, each time at 30% ethylene, 8% oxygen, 5% carbon dioxide and 1400 kPa, the reaction temperature being 260° C., and extrapolating back to zero oxygen conversion.

In the experiment ethylene oxide is produced as follows. A sample of the crushed catalyst (0.8-1.4 mm) is loaded into a micro-reactor consisting of a 3 mm internal diameter stainless steel U-shaped tube. The U-shaped tube is immersed in a molten metal tin/bismuth bath (heat medium) and the ends are connected to a gas flow system. The weight of the catalyst and the inlet gas flow rate are adjusted as to achieve a gas hourly space velocity of 3300 Nl/(l·h). The inlet pressure is 1600 kPa (absolute). The feed to the reactor comprises ethylene at a concentration of 50 mole-%, oxygen at a concentration of 7 mole-%, carbon dioxide at a concentration of 3.5 mole-%, ethyl chloride at a concentration such that the selectivity to ethylene oxide is optimal, and the remainder of the feed is nitrogen. The reaction temperature is 254° C., at which temperature the work rate is 200 kg ethylene oxide/(m³·hr). As the catalyst ages, the reaction temperature is increased gradually such that a constant work rate is maintained. Co-currently with the increase in reaction temperature the concentration of ethyl chloride in the feed is increased in accordance with formula (I), by using B equals $0.22 \times 10^{-6}$.

We claim:

1. A reaction system suitable for performing a process for the epoxidation of an olefin, which reaction system comprises a reactor which is configured to hold a highly selective silver-based catalyst and to receive a feed comprising the olefin, oxygen and a reaction modifier and has a temperature control system configured to control in the reactor a reaction temperature T, which reaction system further comprises a feed control system configured to control the reaction modifier being present in the feed in a relative quantity Q which is the ratio of an effective molar quantity of active species of the reaction modifier present in the feed to an effective molar quantity of hydrocarbons present in the feed, and which reaction system is configured to perform the process steps of:
   operating at a first operating phase wherein the value of T is $T_1$ and the value of Q is $Q_1$, and
   subsequently operating at a second operating phase at a reaction temperature which is different from the reaction temperature employed in the first operating phase, such that the value of T is $T_2$ and the value of Q is substantially $Q_2$, whereby $Q_2$ can be determined by calculation and $Q_2$ is defined by the formula $$Q_2 = Q_1 + B(T_2 - T_1),$$

wherein B denotes a constant factor which is in the range of from $0.01 \times 10^{-6}$ to $1 \times 10^{-6}$ (°C.)$^{-1}$, the relative quantity Q is in the range of from $1 \times 10^{-6}$ to $100 \times 10^{-6}$, and the reaction temperature T is in the range of from 180 to 340° C.

2. A reaction system as claimed in claim 1, wherein the effective molar quantity of active species of the reaction modifier present in the feed can be calculated by multiplying the molar quantity of each of the reaction modifiers present in the feed with a factor, and adding up the multiplication products, wherein each factor represents the number of active heteroatoms present per molecule of the reaction modifier in question, except that the factor for any reaction modifier which is a methyl compound is in the range of from ⅕ to ½.

3. A reaction system as claimed in claim 2, wherein the factor for any reaction modifier which is a methyl compound is in the range of from ⅓.5 to ½.5.

4. A reaction system as claimed in claim 1, wherein the effective molar quantity of hydrocarbons present in the feed can be calculated by multiplying the molar quantity of each of the hydrocarbons present in the feed with a factor, and adding up the multiplication products, wherein the factor for any methane is in the range of from 0 to 0.5; the factor for any ethane is in the range of from 50 to 150; and the factor for any hydrocarbon having at least 3 carbon atoms is in the range of from 10 to 10000, all factors being relative to the factor for ethylene, which equals 1, by definition.

5. A reaction system as claimed in claim 4, wherein the factor for any methane is in the range of from 0 to 0.4; the factor for any ethane is in the range of from 70 to 120; and the factor for any hydrocarbon having at least 3 carbon atoms is in the range of from 50 to 2000, all factors being relative to the factor for ethylene, which equals 1, by definition.

6. A reaction system as claimed in claim 1, wherein the relative quantity Q is in the range of from $2 \times 10^{-6}$ to $50 \times 10^{-6}$.

7. A reaction system as claimed in claim 1, wherein the reaction temperature T is in the range of from 190 to 325° C.

8. A reaction system as claimed in claim 7, wherein the reaction temperature T is in the range of from 200 to 300° C.

9. A reaction system as claimed in claim 1, wherein the value of B, expressed in (°C.)$^{-1}$, is in the range of from $0.1 \times 10^{-6}$ to $0.5 \times 10^{-6}$.

10. A reaction system as claimed in claim 1, wherein
    the effective molar quantity of active species of the reaction modifier present in the feed can be calculated by multiplying the molar quantity of each of the reaction modifiers present in the feed with a factor, and adding up the multiplication products, wherein each factor represents the number of active heteroatoms present per molecule of the reaction modifier in question, except that the factor for any reaction modifier which is a methyl compound is in the range of from ⅕ to ½,
    the effective molar quantity of hydrocarbons present in the feed can be calculated by multiplying the molar quantity of each of the hydrocarbons present in the feed with a factor, and adding up the multiplication products, wherein the factor for any methane is in the range of from 0 to 0.5; the factor for any ethane is in the range of from 50 to 150; and the factor for any hydrocarbon having at least 3 carbon atoms is in the range of from 10 to 10000, all factors being relative to the factor for ethylene, which equals 1, by definition,
    the relative quantity Q is in the range of from $2 \times 10^{-6}$ to $50 \times 10^{-6}$,
    the reaction temperature T is in the range of from 190 to 325° C., and
    the value of B, expressed in (°C.)$^{-1}$, is in the range of from $0.1 \times 10^{-6}$ to $0.5 \times 10^{-6}$.

11. A reaction system as claimed in claim 10, wherein
    the factor for a reaction modifier which is a methyl compound, if present, is in the range of from ⅓.5 to ½.5,
    the factor for any methane is in the range of from 0 to 0.4; the factor for any ethane is in the range of from 70 to 120; and the factor for any hydrocarbon having at least 3 carbon atoms is in the range of from 50 to 2000, all factors being relative to the factor for ethylene, which equals 1, by definition, and the reaction temperature T is in the range of from 200 to 300° C.

12. A reaction system as claimed in claim 1, wherein at the reaction temperature T1 such a value of Q1 is employed that the selectivity towards the olefin oxide formation is optimal.

13. A reaction system as claimed in claim 1, wherein as the catalyst ages, the reaction temperature is changed as to compensate for a reduction in the activity of the catalyst.

14. A reaction system according to claim 1, wherein the highly selective silver based catalyst comprises one or more of rhenium, molybdenum, tungsten, and a nitrate- or nitrite-forming compound, on a support.

15. A reaction system according to claim 1, wherein the reactor holds a highly selective silver based catalyst comprising silver, rhenium or compound thereof, a further metal or compound thereof comprising lithium, potassium and/or cesium and optionally a rhenium co-promoter selected from one or more of sulfur, phosphorus, boron, and compounds thereof.

16. A reaction system according to claim 15, wherein
    the amount of silver is in the range of from 10 to 500 g/kg, calculated as the element on the total catalyst,
    the amount of rhenium is above 1.5 mmole/kg and at most 50 mmole/kg, calculated as the element on the total catalyst, or above 0.0015 mmole/m2 and at most 0.1 mmole/m2, calculated as the element relative to the surface area of the support,
    the amount of further metal or metals is in the range of from 0.1 to 500 mmole/kg each, calculated as the element on the total catalyst, and,
    the amount of any rhenium co-promoter or co-promoters is in the range of from 0.1 to 30 mmole/kg each, calculated as the element on the total catalyst.

* * * * *